United States Patent [19]

Wagner et al.

[11] 4,206,295

[45] Jun. 3, 1980

[54] PROCESS OF PREPARING POLY[{ALKYL-(3-AMMONIOPROPYL-)IMINIO}TRIMETHYLENE DIHALIDES]

[75] Inventors: Arthur F. Wagner, Princeton; Nathaniel Grier, Englewood; Tsung-Ying Shen, Westfield, all of N.J.

[73] Assignee: Merck & Co., Inc., Rahway, N.J.

[21] Appl. No.: 28,933

[22] Filed: Apr. 11, 1979

Related U.S. Application Data

[63] Continuation-in-part of Ser. No. 838,014, Sep. 29, 1977, abandoned, which is a continuation-in-part of Ser. No. 462,263, Apr. 19, 1974, abandoned, which is a continuation-in-part of Ser. No. 369,042, Jun. 11, 1973, abandoned.

[51] Int. Cl.$^2$ .............................................. C08L 79/00
[52] U.S. Cl. ...................................... 525/410; 424/78; 525/411; 525/414; 525/417; 528/408
[58] Field of Search ............... 528/367, 404, 422, 423; 525/410, 411, 417, 414

[56] References Cited

U.S. PATENT DOCUMENTS

| | | | |
|---|---|---|---|
| 2,884,057 | 4/1959 | Wilson et al. | 528/423 |
| 3,308,020 | 3/1967 | Wolf et al. | 167/65 |
| 3,354,103 | 11/1967 | White | 528/423 |
| 3,372,129 | 3/1968 | Phillips | 528/422 |
| 3,821,125 | 6/1974 | Saegusa et al. | 528/422 |
| 3,833,521 | 9/1974 | Korbstein et al. | 528/404 |

FOREIGN PATENT DOCUMENTS 396351  2/1974  U.S.S.R.

*Primary Examiner*—Wilbert J. Briggs, Sr.
*Attorney, Agent, or Firm*—Harry E. Westlake, Jr.; Walter Patton

[57] ABSTRACT

Novel polymers having a linear backbone which is free from both branching and cross-linking, comprising quaternized nitrogen atoms linked to each other through trimethylene groups. By the term "linear backbone" is meant that the polymer has only acyclic groups, i.e. trimethylene, linking the nitrogen atoms in a single continuous chain; the polymer is free from "branching" when it has no repeating monomer units extending from the polymer backbone; and it is free from "cross-linking" when there is no joining of two linear backbones. These polymers are useful as antimicrobials, flocculating agents, antistatic agents, electroconductive agents for coating paper, chelating agents and bile acid binding agents, as well as in similar applications where their high charge to weight ratio and fully accessible nitrogen atoms can be employed. The polymers are obtained by the polymerization of dihydro-oxazine, reductive alkylation of the resulting polymer, followed by quaternization.

15 Claims, No Drawings

PROCESS OF PREPARING POLY[{ALKYL-(3-AMMONIOPROPYL)IMINIO}-TRIMETHYLENE DIHALIDES]

This is a continuation-in-part of copending application of Ser. No. 838,014, filed Sept. 29, 1977, now abandoned which is a continuation-in-part application of copending application Ser. No. 462,263, filed Apr. 19, 1974, now abandoned, which is a continuation-in-part of copending application Ser. No. 369,042, filed June 11, 1973, now abandoned.

DISCLOSURE OF THE INVENTION

This invention relates to novel polymers, together with methods for their preparation. More particularly, this invention relates to polymers derived from dihydro-oxazines which have a linear backbone free from both branching and cross-linking, comprising either tertiary or quaternized nitrogen atoms linked to each other through trimethylene groups.

These polymers are advantageously employed as antimicrobials, flocculating agents, electroconductive agents in paper coatings, antistatic agents, chelating agents, and bile acid binding agents, as well as in similar applications where their high charge to weight ratio, and the accessibility of their charged nitrogens, can advantageously be employed.

They are active as nonabsorbable gastrointestinal bile acid binding agents, which binding is known to reduce levels of blood serum cholesterol. Available evidence indicates that the incidence of higher than normal blood serum cholesterol levels in humans is associated with atherosclerosis and other hypercholesteremic disease signs, which can result in occlusion of the circulation, giving rise to coronary, cerebrovascular, and some forms of peripheral vascular diseases.

Heretofore, a variety of bile acid binding agents have been employed. These include iron salts which produce insoluble precipitates with bile acids, organic bases to act similarly, and polymers having a salt-forming capability. Absorbable precipitants, however, present acute and chronic toxicity hazards. The use of non-absorbable polymers to avoid such toxicity problems has not provided a suitable alternative, because the average effective adult daily dose of such polymers heretofore employed ranges up to 40 grams. The physical bulk of such a dose, especially when of a water-insoluble cross-linked resin, can induce partial blockage of the gastrointestinal tract and an unpleasant, heavy sensation. Furthermore, any objectionable odor and taste of so large a dose is difficult to mask. There has therefore been only limited benefit derived from treatment using these prior bile acid binding agents, although the incidence of disease linked to hypercholesteremia is extremely high and continues to rise alarmingly.

We have now found that the novel linear, unbranched polymers hereinafter described are exceptionally effective in binding or sequestering bile acids in the gastrointestinal tract, and in lowering blood serum levels of cholesterol. That the polymers of this invention are linear and unbranched is critical to the advance made by this invention. Thus, while some references, e.g., U.S. Pat. No. 3,308,020 disclose monomer units that are similar to the monomer units herein disclosed, these prior art polymers, by virtue of the materials and methods used to prepare them, are highly branched.

The polymers of this invention are represented by the formula I

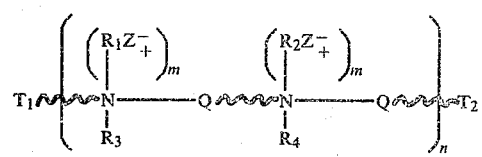

wherein $R_1$ and $R_2$ are the same or different and are hydrogen; lower($C_1$ to $C_4$)alkyl; hydroxy-substituted $C_1$ to $C_4$ alkyl, polyhydroxy-substituted $C_3$ to $C_6$ alkyl and polyhydroxysubstituted $C_3$ to $C_7$ cycloalkyl; $C_3$ to $C_7$ cycloalkyl; $C_3$ to $C_7$ cycloalkyl-substituted loweralkyl; loweralkyl-substituted $C_3$ to $C_7$ cycloalkyl; ammonioloweralkyl; loweralkylammonioloweralkyl; diloweralkylammonioloweralkyl; triloweralkylammonioloweralkyl; carboxyloweralkyl; carboloweralkoxyloweralkyl; $C_3$ to $C_7$ alkenyl; $C_3$ to $C_7$ alkynyl; aralkyl, e.g., 2(1-naphthyl)ethyl, benzyl; carbamyloweralkyl; fluoroloweralkyl, e.g., ω-trifluoroloweralkyl; cyanoloweralkyl; guanidinoloweralkyl; carbamidinoloweralkyl; N-loweralkylcarbamidinoloweralkyl; loweralkoxyloweralkyl; loweralkylthioloweralkyl; furanosyl; pyranosyl, e.g., α-D-glucopyranosyl; and loweralkanoyloweralkyl; but only one of $R_1$ and $R_2$ is lower alkyl.

$R_3$ and $R_4$ are alike or different and are lower($C_1$ to $C_4$)alkyl; monohydroxy-substituted $C_1$ to $C_4$ alkyl, polyhydroxy-substituted $C_3$ to $C_6$ alkyl and polyhydroxy-substituted $C_3$ to $C_6$ cycloalkyl; $C_3$ to $C_7$ cycloalkyl; $C_3$ to $C_7$ cycloalkyl-substituted loweralkyl; loweralkyl-substituted $C_3$ to $C_7$ cycloalkyl; ammonioloweralkyl; loweralkylammonioloweralkyl; diloweralkylammonioloweralkyl, triloweralkylammonioloweralkyl; carboxyloweralkyl; carboloweralkoxyloweralkyl; $C_3$ to $C_7$ alkenyl; $C_3$ to $C_7$ alkynyl; aralkyl, e.g., 2(1-naphthyl)ethyl, benzyl; carbamyloweralkyl; fluoroloweralkyl, e.g., ω-trifluoroloweralkyl; cyanoloweralkyl; guanidinoloweralkyl; carbamidinoloweralkyl; N-loweralkylcarbamidinoloweralkyl; loweralkoxyloweralkyl; loweralkylthioloweralkyl; furanosyl; pyranosyl, e.g., α-D-glucopyranosyl; and loweralkanoyloweralkyl.

n is an integer such that the number average molecular weight is from 300–50,000;

m is 0 or 1;

$Z^-$ is a monovalent or polyvalent counter anion;

Q is trimethylene; and the symbol ⌇ indicates a bond to a plurality of the groups

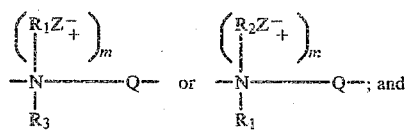

where Q, $Z^-$, m, $R_1$, $R_2$, $R_3$ and $R_4$ have their previously defined meanings.

$T_1$ and $T_2$ are terminal groups on the polymer. The exact nature or identity of these terminal groups $T_1$ and $T_2$ is immaterial to the invention, or to the utility of the presently invented polymers, since the large number of monomer components in the polymer chain are necessarily the major determinants of the chemical and physical properties of the polymer. However, in the polymers made starting with dihydro-oxazine, and depending on the solvent (aqueous or alcoholic) wherein opening of the dihydro-1,3-oxazine ring is effected, $T_1$ is $R_5(R_3)$ $(R_1Z^-)m$ $N^{(+)}m$—Q—, and $T_2$ is —$N^{(+)}m(R_1Z^-)_m$ $(R_3)$ —Q—OR* or a dihydro-1,3-oxazinium complex with an anion of the initiator; where $R_1$, $R_3$, $Z^-$, m and Q have their previous meanings, $R_5$ is selected from the same group as $R_1$ and $R_3$, but may be the same or different from either one or both of $R_1$ and $R_3$, and R* is a fragment derived from the solvent wherein the ring opening was effected, e.g., R* is hydrogen if an aqueous treatment was employed, or lower alkyl such as methyl or ethyl, if an alcohol treatment was employed.

In polymers of formula I made by polymerization of an appropriate monomer or monomers, $T_2$ is —$N^+(R_1Z^-)$ $(R_3)$—W, where $R_1$, $R_3$ and $Z^-$ have their previous meanings, and W is allyl, hydroxypropyl or halopropyl, the latter being preferably converted to propyl, alkoxypropyl, ammoniopropyl, (alkyl, dialkyl or trialkyl)ammoniopropyl or arylthiopropyl, and $T_1$ is allyl, hydroxypropyl, N-alkyl-N-[3-(N',N',N'-trialkylammonio)propyl]-3-aminopropyl or halopropyl, the latter being preferably converted to propyl, ammoniopropyl or (alkyl, dialkyl or trialkyl)ammoniopropyl.

In a preferred embodiment, the polymer has the structure indicated in formula II below:

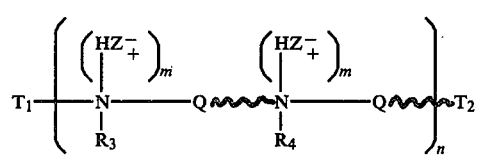

where ⁓indicates bonding to one or more groups

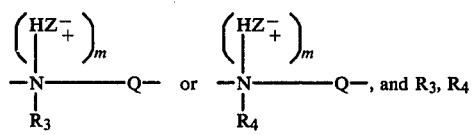

$Z^-$, $T_1$, $T_2$, Q, m and n have their previously defined meanings.

In another preferred embodiment, the polymer has the structure indicated in formula III below:

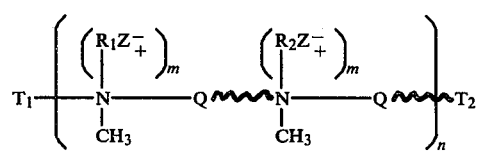

where ⁓indicates bonding to one or more groups

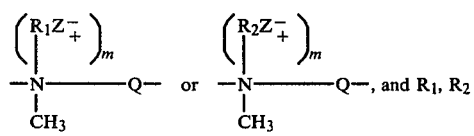

$Z^-$, $T_1$, $T_2$, Q, m and n have their previously defined meanings.

Throughout this description, $Z^-$ represents an anion which counters the charge on the quaternized or protonated imino group, and thus can be a monovalent anion. It is to be understood, however, that Z is contemplated to include polyvalent anions where one anion can counter the charge on more than one charged imino group. Thus, $Z^-$ can include anions of inorganic acids, as well as from organic acids such as, for example, halide, e.g., chloride, bromide, or iodide; sulfate; bisulfate; phosphate; acetate; ascorbate; citrate; hydroxycitrate; carbonate; bicarbonate; nicotinate; glycinate; taurinate; salicylate; and other anions derived from physiologically non-toxic acids, especially salts of physiologically active acids such as those derived from clofibrate and halofenate, i.e., 2-(p-chlorophenoxy)-2-methylpropionic and 3-trifluoromethylphenoxy-(4-chlorophenyl) acetic acids. When such anions of physiologically active compounds are used to neutralize quaternized or protonated imino groups, it is apparent that only a portion of the charged imino groups may be so neutralized. The proportion of anion from the physiologically active compound is adjusted so that the amount administered with the polymer dosage falls within the desired range for the physiologically active compound.

The polymers of this invention are obtained through a sequence of steps, the first of which is the polymerization of a 5,6-dihydro-4H-1,3-oxazine of the formula:

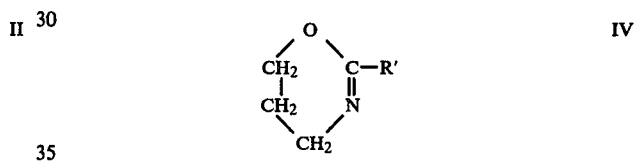

where R' is hydrogen or loweralkyl.

STEP 1—Polymerization

The polymerization of the 2-R'-5,6-dihydro-4H-1,3-oxazine is known and is reported in *Macromolecules*, 6, 495 (1973). The preferred initiator is methyl iodide; from 0.005 to 0.1 moles of methyl iodide is used for each mole of 2-R'-5,6-dihydro-4H-1,3-oxazine, with 0.02 mole of methyl iodide per mole of 2-R'-5,6-dihydro-4H-1,3-oxazine being preferred.

Generally, the polymerization of the 2-R'-5,6-dihydro-4H-1,3-oxazine is carried out in a closed system in an inert solvent and under an inert atmosphere such as nitrogen at a pressure of from 1-100 atmospheres and heating to from 30° C. to 120° C. for a period of from 1-12 hours. By inert solvent, it is meant here and elsewhere in this specification, a solvent which is not reactive under these conditions either with reactants, products or itself, dimethylformamide here being the preferred solvent.

After reaction is complete, the polymerization reaction mixture, now comprising the polymer V

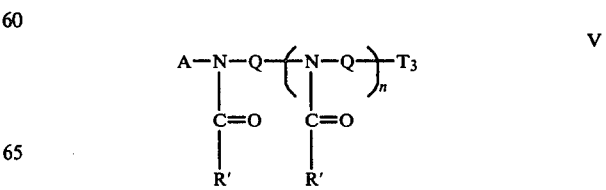

where R', Q and n are as previously defined and $T_3$ is

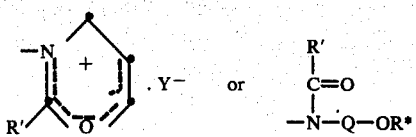

where y is an anion from the initiator, A is hydrogen or an initiator fragment such as methyl from methyl iodide and Q and R* are as previously defined, is treated with an anhydrous solvent preferably an alcohol or ether such as methanol or ethyl ether. After filtration and washing with anhydrous solvent, the polymer is collected and dried.

After isolation, the polymer is next subjected to either one of three alternative second steps: hydrolysis; direct reduction; or reductive methylation.

STEP 2A—Hydrolysis

The hydrolysis which cleaves the acyl group is carried out by reacting the polymer V with an aqueous acid such as aqueous mineral acid, e.g., hydrochloric acid, or a base such as alkali hydroxide giving the polymer VI

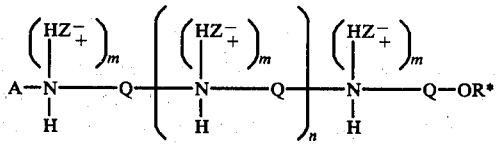

VI where A, m, Q, $Z^-$, R*, and n have their previous meanings, and $Z^-$ is preferably a halide.

The alkaline hydrolysis is accomplished by admixing the polymer with an aqueous solution of from saturated to b 0.1 N base, suitably alkali hydroxide and preferably sodium hydroxide. The acid hydrolysis is carried out in 1 to 2 N aqueous mineral acid, e.g., HCl or $H_2SO_4$.

The hydrolysis is conducted with agitation and warming for at least 3 to 30 hours. Preferably, to achieve substantially complete hydrolysis at a slight sacrifice in molecular weight, the hydrolysis can be carried out in a sealed vessel at a temperature of from 40° C. to 180° C. The quantity of aqueous hydrolyzing solution is not critical, provided that agitation is good and at least twice the theoretical amount of alkali or acid is employed to effect the hydrolysis.

From the base hydrolysis, polymer VI is obtained where m is 0, and the acid hydrolysis or subsequent acidification of the base hydrolyzed polymer gives polymer VI where m is 1.

STEP 2B—Direct Reduction

Polymer V is reduced directly to polymer VII by reduction of the acyl group.

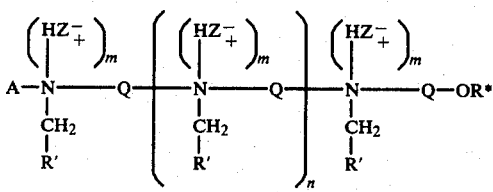

VII where A, $Z^-$, Q, R', R*, m and n are as previously defined.

Preferably, the polymer is dissolved in an inert solvent and slowly admixed with at least a molar equivalent of a chemical reductant such as diborane which also is dissolved in an inert solvent. The preferred solvents are tetrahydrofuran and mixtures thereof with ethyleneglycol dimethyl ether. After addition, the reaction mixture is refluxed for 1-12 hours, cooled and acidified. Other reducing agents which can be employed in place of the diborane include aluminum hydride, lithium aluminum hydride, and lithium trimethoxy aluminum hydride.

Alternatively, the amide groups of polymer V are converted by alkylation to imino esters with triethyloxonium tetrafluoroborate complex in methylene chloride at 25° C. The imino ester moieties are then readily reduced to tertiary amine moieties as with sodium borohydride in ethanol at 0° C. to 25° C.

STEP 2C—Reductive Methylation

In this procedure polymer V where R' is hydrogen is heated with a mixture of more than one equivalent each of formaldehyde and formic acid, then treated with an aqueous acid and concentrated to dryness under reduced pressure to give polymer VIII.

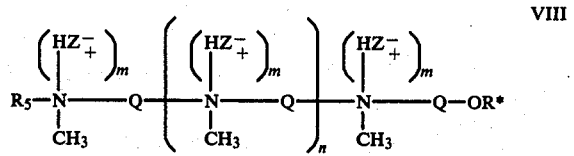

VIII where $R_5$, Q, $Z^-$, R*, m and n have their previous meanings.

The polymer to be reductively methylated is added to a mixture of 97% to 100% formic acid and preferably 38% aqueous formaldehyde, and the reaction mixture heated to a temperature of from 30° C. to 100° C. for a period of from 20 to 100 hours. Although higher reaction temperatures are not prohibited, the increased rate of thermal decomposition of formic acid and the risk of degradation of the polymer make the use of higher temperatures less attractive. The mixture is then treated with an aqueous mineral acid, preferably hydrochloric acid, and the excess formic acid, formaldehyde and mineral acid are removed by concentration under reduced pressure.

STEP 3—Direct Methylation

Polymer VI where m is 0 is methylated directly by heating the polymer in a mixture of more than one equivalent each of formaldehyde and formic acid under conditions described in Step 2C to yield polymer VIII where $R_5$, Q, $Z^-$, R*, m and n have their previous meanings.

STEP 4—Addition of $R_3$ and $R_4$ to Polymer VI

For polymers of formula IX below in which $R_3$ and $R_4$ are the same, polymer VI where m is 0 is treated with an excess (from 1.5-8 equivalents, and preferably 4 equivalents) of an alkylating agent RX in an inert solvent at temperatures ranging from 30° C. to 100° C. The reaction is carried out by dissolving the polymer in an inert solvent such as alcohols, ketones, or dimethylformamide. Preferred solvents include methanol, acetone and dimethylformamide, and preferred temperatures are between 50° C. to 75° C. This results in a polymer of formula IX in which A, Q, $Z^-$, $R_3$, $R_4$, $R^*$ and n have their previous meanings and m is 1 and $Z^-$ is $X^-$. Treatment of polymer IX with exactly one equivalent of base yields polymer IX in which m is 0.

For polymers of formula IX in which $R_3$ and $R_4$ are different, polymer VI where m is 0 is treated with less than an equivalent amount of an alkylating agent $R_3X$ and then after neutralization with a matching equivalent of base the intermediate is treated with sufficient $R_4X$ to complete alkylation. Both reactions are conducted in an inert solvent at temperatures ranging from 30° C. to 100° C. The reactions are conducted by dissolving the polymer in an inert solvent such as alcohols, ketones or dimethylformamide. Preferred solvents include methanol, acetone and dimethylformamide, and preferred temperatures are between 50° C. to 75° C. Acid neutralization forms polymer IX in which A, Q, $Z^-$, $R^*$ and n have their previous meanings and m is 1, and $Z^-$ is $X^-$. Treatment of polymer IX with exactly one equivalent of base yields polymer IX in which m is 0.

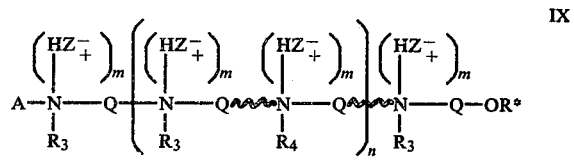

IX where A, $Z^-$, Q, $R_3$, $R_4$, $R^*$, m and n are as previously defined.

STEP 5—Quaternization—Addition of $R_1$, $R_2$

Polymer VII from Step 2B, polymer VIII from Step 2C or Step 3, or polymer IX from Step 4, usually obtained as their acid addition salts (m=1), are converted to the free base form (m=0) on treatment with an equivalent amount of base. At this stage, it is convenient, though not necessary to remove any inorganic salts by ultrafiltration techniques. This has the added advantage of also eliminating any other undesirable lower molecular weight material. The aqueous solution of the polymer is then concentrated under reduced pressure and the product is dried prior to the quaternization reaction (when that reaction is conducted in non-aqueous solvent), which reaction leads to polymers of formula I. The quaternization reaction is, however, not only conducted in inert non-aqueous solvents such as alcohols, ketones or dimethylformamide, preferably methanol, acetone or dimethylformamide, but is often advantageously carried out in aqueous solution, such as water alone, or mixtures of water-methanol, water-acetone or water-dimethylformamide. The quaternizing agents are usually halogen containing compounds, preferably bromo compounds. Other alkylating agents such as toluenesulfonate esters or trichloromethylsulfonate esters can also be employed. When $R_1$ and $R_2$ are the same, a reasonable excess of the alkylating agent RX is employed; when $R_1$ and $R_2$ are different, the polymer is first treated with a limiting amount (5% to 95% of equivalence) of $R_1X$. After that reaction is complete, the product is treated with an excess of reagent $R_2X$. When the alkylating reactivities of the reagent $R_1X$ and $R_2X$ are the same, the reaction may be carried out in a mixture of $R_1X$ and $R_2X$ in a single step. The $R_1X$ and $R_2X$ may be simple alkyl halides or may also carry other functional groups which do not interfere with the quaternization reaction. A simple but by no means exhaustive list of acceptable quaternization reagents includes haloalkyl acid esters, haloalkyl acid amides, haloketones, 3-bromo-1-chloro-propane, alkyl halohydrins, aralkyl halides, mono, di and tri-loweralkyl-substituted ammonioalkyl halides, alkoxyalkyl halides, alkylthioalkyl halides, allyl halides, and propargyl bromide.

The reaction is conducted by allowing a solution of starting polymer VII, VIII or IX and alkylating agent in water, methanol, dimethylformamide, or mixtures thereof, to stand at 25° C. to 100° C. for three hours to several days depending on the temperature employed and the reactivity of the alkylating agent. The polymer product of formula I thus formed, when insoluble in the reaction mixture, is conveniently isolated directly by filtration; in some instances, it is expedient to dilute the reaction mixture with several volumes of a non-solvent for the polymer prior to isolation; when the polymer I is soluble in the reaction-mixture, the volatile components are ordinarily evaporated under reduced pressure to give the polymer as a residual solid. The polymer is usually partially dried, ground to a powder and then dried under reduced pressure at temperatures of from 25° C. to 60° C.

STEP 6—Ion Exchange

When polymer I is prepared by the techniques of the prior steps, the anions $Z^-$ of the polymer I are generally halides. The full range of polymers of formula I where the anion $Z^-$ differs from halide can be obtained by dissolving polymer I, having a halide anion, in water, alcohol, or mixtures thereof in any proportion and passing the solution through a bed of anion exchange resin, either a synthetic or a zeolite type, where the halide ion is exchanged and replaced by the desired $Z^-$. The anion-exchange method employing a resin technique can be direct, that is, exchanging halide ion for $Z^-$ or one can first exchange halide ion for $OH^-$ and then, either by a subsequent ion exchange or simple neutralization, exchange $OH^-$ for $Z^-$.

Additionally, chemical exchange techniques can be employed when a precipitate of a metal halide is less soluble than the added metal salt MZ. The precipitated metal halide can then be filtered from the soluble polymer I.

A simple example of the latter technique involves treating a solution of polymer I containing the bromide counter ion with an excess of freshly precipitated silver chloride. After the halide anion exchange is complete, the mixture of silver chloride and silver bromide is removed by filtration leaving a solution of polymer I containing the chloride counter ion. Alternatively, polymer I where Z is sulfate can be treated with solutions of water soluble calcium or barium salts. Thus, sulfate can be replaced with nitrate and the precipitate of barium sulfate removed.

A preferred polymer of this invention, poly[{methyl-(3-trimethylammoniopropyl)iminio}*trimethylene dihalide], which is represented by formula I where Q is trimethylene, m is 1, $R_3$ and $R_4$ are both methyl and $R_1$ and $R_2$ are both 3-trimethylammoniopropyl, and $Z^-$ is a halide anion, has the structure indicated by formula X below:

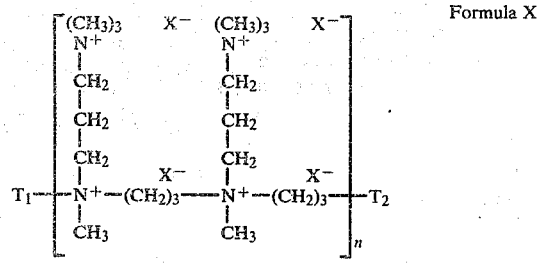

Formula X wherein $X^-$ is a halide anion, and $T_1$ and $T_2$ are as previously defined. This poly-[{methyl-(3-trimethylammoniopropyl)iminio}trimethylene dihalide[ is prepared, in accordance with the quaternization procedure described hereinabove under the heading Step 5, by reacting the alkylating agent, 3-bromopropyltrimethylammonium bromide, with poly[methylimino)trimethylene]; the latter polymer is represented by formula VIII where Q is trimethylene and m is 0, and may be specifically represented by the structure indicated in formula XI below:

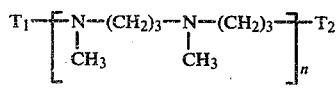 XI wherein $T_1$ and $T_2$ are as previously defined.

*This designation "iminio", which is used here and in the claims, is preferred Chemical Abstracts nomenclature; the term "imino", which is also sometimes used in this specification (e.g. working examples), as well as in parent Ser. No. 462,263, to designate the linear quaternary nitrogen, accords with IUPAC nomenclature.

The anions on the polymers of formulas I and X are generally halide as a result of the techniques of the prior steps. The full range of polymers where the anion differs from halide are obtained by dissolving the polymer of formulas I or X having a halide anion in water, alcohol, or mixtures thereof in any proportion and passing the solution through a bed of anion exchange resin, either a synthetic or a zeolite type, where the halide ion is exchanged and replaced by $Y^a$ where Y is a pharmaceutically acceptable anion and a is the anionic charge on Y. The anion exchange method employing a resin technique can be direct, that is, exchanging halide ion for $Y^a$ or one can first exchange halide ion for $OH^-$ and then either by a subsequent ion exchange or simple neutralization, exchange $OH^-$ for $Y^a$.

Additionally, chemical exchange techniques can be employed when a precipitate of a metal halide is less soluble than the added slightly soluble metal salt MY. The precipitated metal halide can then be filtered from the soluble polymer of formulas I or X.

A simple example of the latter technique involves treating a solution of the polymer of formulas I or X containing the bromide counter ion with an excess of freshly precipitated silver chloride. After the halide anion exchange is complete, the mixture of silver chloride and silver bromide is removed by filtration leaving a solution of the polymer containing the chloride counter ion.

Throughout this description, $Y^a$ represents an anion which counters the charge on the quaternized imino group, and thus can be a monovalent anion. It is to be understood, however, that $Y^a$ is contemplated to include polyvalent anions where one anion can counter the charge on more than one charged imino group. Thus, $Y^a$ can include anions of inorganic acids, as well as of organic acids such as, for example, halide, e.g., chloride, bromide, or iodide; sulfate; bisulfate; phosphate; acetate; ascorbate; citrate; hydroxycitrate; carbonate; bicarbonate; nicotinate; glycinate; taurinate; salicylate; and other anions derived from physiologically non-toxic acids, especially salts of physiologically active acids such as those derived from clofibrate and halofenate, i.e., 2-(p-chlorophenoxy)-2-methylpropionic and 3-trifluoromethylphenoxy-(4-chlorophenyl)acetic acids. When such anions of physiologically active compounds are used to neutralize quaternized imino groups, it is apparent that only a portion of the charged imino groups may be so neutralized. The amount of anion from the physiologically active compound is apportioned in a ratio such that the amount administered with the polymer dosage can fall within the desired range for the physiologically active compound.

Effective lowering of cholesterol blood levels is obtained by the oral administration of remarkably small dosages of the polymers of this invention. This enables a flexibility of formulation previously unavailable. The polymers can be finely divided powders and suitably used as such or preferably admixed with varying amounts of solid carrier agents such as colloidal silica, starches, sucrose, talc, lactose, cellulose, or modified cellulose, dry milk powder, protein powders such as soy flour, and the like. These are preferably made into unit dosage forms such as tablets, filled gelatin capsules or a foil or paper envelope containing the premeasured dose which can include supplementary vitamins and minerals, and which can be readily torn open and added to edible liquids such as fruit juices or other beverages. The unit dose composition may comprise from 10% to 99% by weight of polymer, the remainder being carriers, flavorings, excipients, flow agents and the like. In such a unit dose, the active polymer may comprise from 0.1 gm. to up to 10 gms. in powder packets.

Also suitable are aqueous solutions or suspensions which can be prepared and are preferably sweetened or flavored. Although not entirely desirable, the polymers can be mixed in various vehicles such as safflower or corn oil for oral ingestion as such or as an aqueous emulsion. These may also be encapsulated.

The total daily dosage of bile acid binding polymer is preferably divided into three or four equal portions and taken before each meal and prior to bedtime. This regimen provides for maximum resin contact time during periods of highest intestinal bile acid concentrations.

The polymers of this invention may be used alone, or, if desired, can be compounded together with triglyceride synthesis inhibitors or other bile acid binding agents for particular treatments. In addition, as heretofore stated, the polymers described herein form salts with the acids of clofibrate and halofenate, which salts are useful in cardiovascular disease therapy. The following examples are illustrative of the dosage forms which can be employed in the practice of our invention. Those skilled in the art of pharmaceutical compounding will be aware of variations which can be practical without departing from the spirit of our invention. It is anticipated that multiple dosages, e.g., two or three tablets or capsules can be taken at one time if higher dosages are prescribed.

Additional ingredients which may comprise the carrier portion of the compositions of this invention, can also have pharmacological activity and can include other choleretic agents such as tocamphyl florantyrone;

taurine; and glycine; hypocholesteremic agents such as nicotinic acid; the D-isomer of 3,3',5-triiodothyronine; thyroxine-like compounds such as sodium L-thyroxin and sodium D-thyroxine; triiodothyropropionic acid; nafoxidine hydrochloride, 5-methylpyrazole-3-carboxylic acid and 3-methyl-5-isoxazolecarboxylic acid; fecal softeners such as poloxalkol and dioctyl sodium sulfosuccinate; as well as unsaturated fatty acids such as linoleic acid, arachidonic acid and linolenic acid. Although not preferred, edible vegetable oils such as corn oil and safflower oil are also suitable.

POWDER PACKETS

Linear, unbranched and non-cross-linked poly[{methyl-(3-trimethylammoniopropyl)imino}trimethylene dichloride] is finely powdered and blended with 1% by weight of lactose powder. Aluminum envelopes containing a paper bag liner are individually filled with 0.55 g. of the mixture and sealed against moisture to prevent caking.

HARD GELATIN CAPSULES

A 250 mg. dose of poly-[{methyl-(3-trimethylammoniopropyl)imino}trimethylene dichloride] containing 1% by weight of lactose as described above is filled into the appropriate size hard gelatin capsules.

Alternatively, a dry filled capsule can be prepared from the following components:

| | |
|---|---|
| poly-[{(methyl-3-trimethylammoniopropyl)imino}-trimethylene dichloride] | 300 mg. |
| corn starch | 150 mg. |
| cab-o-sil (anhydrous silica) | 5 mg. |

If capsules of lower potency are to be prepared, the capsule size can be decreased or additional corn starch or other diluent employed. When using smaller amounts of active ingredient it is anticipated that a multiple capsule dose can be administered.

COMPRESSED TABLETS

A dry blend is prepared with the following components:

| | |
|---|---|
| poly-[{(methyl-(3-trimethylammoniopropyl) imino}-trimethylene dichloride] | kg. |
| sucrose, powdered | 30 gms. |
| colloidal silica | 10 gms. |
| carbowax-4000 | 30 gms. |

Four thousand tablets are pressed therefrom by direct compression each of which tablets contains 250 mg. of the ionene polymer.

Likewise, compressed tablets are prepared such that each tablet contains:

| | |
|---|---|
| poly-[{(methyl-3-trimethylammoniopropyl)imino}-trimethylene dichloride] | 300 mg. |
| corn starch | 30 mg. |
| polyvinylpyrrolidone | 10 mg. |
| magnesium stearate | 3 mg. |

After tableting, a plastic film can be applied to the tablets to seal them from moisture in ways well known in the art.

In addition, an enteric coating may be applied, if desired. Such a coating may comprise fats, fatty acids, waxes and mixtures thereof, shellac, ammoniated shellac, and cellulose acid phthalates applied by techniques well known and accepted.

In place of the poly-[{(methyl-3-trimethylammoniopropyl)imino}trimethylene dichloride], there may be substituted the other polymer salts of our invention.

Other binding agents may be used in place of sucrose, such as dextrose, lactose, methyl cellulose, natural and synthetic gums, and the like. Talc can replace the calcium or magnesium stearate. A variety of readily available non-toxic anti-caking agents may be substituted for the colloidal silica.

Other lubricants, diluents, binders, coloring agents, flavoring agents and disintegrators can be used as are known in the art employing wet or dry granulation techniques, direct compression, spray drying, and the like.

If desired, a chewable tablet can be prepared from preferably microencapsulated polymer particles by dry granulation as follows:

| | |
|---|---|
| microencapsulated poly-[{(methyl-(3-trimethyl-ammoniopropyl)imino}trimethylene dichloride] | 750 mg. |
| mannitol | 300 mg. |
| sodium saccharine (or other sweetener) | 2 mg. |
| oil of peppermint | 1 mg. |
| carbowax-4000 | 15 mg. |
| microcrystalline cellulose | 100 mg. |

All of the above dosage forms are administered orally in an effective bile acid binding dose. For lowering blood serum cholesterol levels, generally single or multiple dose of from about 0.1 to 5.0 grams is suitable although doses in excess of 10 grams can be given where indicated. Such doses are also effective in relieving symptoms of biliary pruritus. Administration can be in a variety of forms, such as a suspension, in an aqueous solution, as a chewable or a coated tablet, or in a capsule, and can be continued for an extended course of treatment. Generally, medication is on a daily basis with each day's dose taken in divided portions, preferably with meals.

For control of hypercholesterolemia, the particular individual dosage, given variances in metabolism and diet, is preferably arrived at through an initial determination and continued monitoring of blood serum cholesterol levels. Thus, a moderate dosage might be employed initially, and increased until the desired blood serum cholesterol level is achieved and maintained. For an initial dose, pending such individual adjustment, from 2.5 to 100 mg./kg. of body weight per day is satisfactory.

It is contemplated that acid addition salts of the polymers of formulas I and X, including those salts derived from the acids $H_{1/m}Y^a$ where Y, m and a are as above defined are equally well suited for the uses heretofore described.

The following examples are included as illustrative of the invention and are not intended to limit the scope of the invention as described in the foregoing specification and claims.

EXAMPLE 1

5,6-Dihydro-4 H-1,3-oxazine

A mixture of 94 g. (1.13 moles) of t-butyl isonitrile, 85 g. (1.13 moles) of freshly distilled 3-aminopropanol, and 7.4 g. (0.055 mole) of silver cyanide is stirred at 90° C. under a nitrogen blanket for 16 hours. The product is isolated from the reaction mixture by distillation at 45 mm. and is purified by repeated fractionation. Usually, two such fractionations suffice to yield a pure product. In this manner, 44 g. of pure 5,6-dihydro-4 H-1,3-oxazine, b.p. 58° C./ 58 mm., $n_D^{25}$ 1.4485 is obtained and stored over molecular sieves type 4 A and under nitrogen.

EXAMPLE 2

Poly-[(Formimino)trimethylene]

A solution of 44 g. (0.52 mole) of 5,6-dihydro-4 H-1,3-oxazine in 140 ml. of purified dimethylformamide is put in a pressure tube and 1.52 g. (0.011 mole) of iodomethane is added. The system is purged with nitrogen, sealed and heated at 80° C. for five hours. The mixture is cooled and diluted with ten volumes of ether, and the product is isolated by filtration. The product is washed with ether and dried under reduced pressure at 75° C. yielding 40 g. of poly[(formimino)trimethylene], m.p. decomposes at 111° C.–112° C.

EXAMPLE 3

Poly-[(Methylimino)trimethylene Hydrochloride]

A mixture of 53 g. of poly-(formiminotrimethylene), 1320 g. of 97%–100% formic acid, and 308 g. of 38% aqueous formaldehyde is heated at 100° C. for 120 hours. After the solution is cooled, 650 ml. of concentrated hydrochloric acid is added, and the mixture is concentrated to dryness at 50° C. under reduced pressure. The residue is triturated with 400 ml. of methanol, isolated by filtration, washed with ether and dried under reduced pressure yielding 67 g. of poly-[(methylimino)trimethylene hydrochloride].

EXAMPLE 4

Poly-[(Methylimino)trimethylene]

A solution of 67 g. (630 milliequiv.) of poly[(methylimino)trimethylene hydrochloride] in 600 ml. of water is treated with 39 g. (0.72 mole) of sodium methoxide. This is simply an easy way to prepare a solution of sodium hydroxide of precise normality. A corresponding volume of a standardized solution of sodium hydroxide is equally adequate. The solution is desalted and polymer with molecular weight below 1,000 is removed using an Amicon filter cell equipped with a UM2 Diaflo Ultrafilter. Finally, the solution is concentrated at 50° C. under reduced pressure yielding 45 g. of poly-[(methylimino)trimethylene].

EXAMPLE 5

Poly-[(Dimethylimino)trimethylene Bromide]

A solution of 14 g. (200 milliequiv.) of poly[(methylimino)trimethylene] and 76 g. (0.8 moles) of bromomethane in 90 ml. of methanol is heated at 50° C. in a sealed reactor for five hours. The product is isolated by filtration, washed with methanol and then ether, and dried under reduced pressure, yielding 28 g. of poly-[(dimethylimino) trimethylene bromide].

EXAMPLE 6

Poly-[(Dimethylimino)trimethylene Chloride]

A solution of 28 g. (170 milliequiv.) of poly[(dimethylimino)trimethylene bromide] in 1400 ml. of water is passed slowly through a column containing 1,000 ml. of Dowex 1–X2 (Cl− cycle) resin (0.8 mole). After the solution has passed through, water is passed through the column until a negative silver nitrate test is observed with the effluent. The total effluent is concentrated to dryness, and the product is dried under reduced pressure yielding 17.2 g. of poly-[(dimethylimino)trimethylene chloride].

EXAMPLE 7

Poly-[{Methyl-(3-hydroxypropyl)imino}trimethylene Bromide]

A solution of 142 mg. (2 milliequiv.) of poly[(methylimino)trimethylene] and 1.12 g. (8 mmoles) of 3-bromopropanol in 5 ml. of purified dimethylformamide is heated at 75° C. for 24 hours. The product is isolated by filtration, washed with acetone and dried under reduced pressure yielding 330 mg. of poly-[{methyl-(3-hydroxypropyl)imino}trimethylene bromide].

EXAMPLE 8

Poly-{(Methyl-(3-hydroxypropyl)imino}trimethylene Chloride

A solution of 315 mg. (1.5 milliequiv.) of poly[{methyl-(3-hydroxypropyl)imino}trimethylene bromide] in 16 ml. of water is passed slowly through a column of 9 ml. of Dowex 1–X2 ion exchange resin (7.2 mmoles chloride ion), and then water is passed through until the effluent gives a negative test for chloride ion. The combined effluent is concentrated to dryness at 50° C. under reduced pressure yielding poly-[{methyl-(3-hydroxypropyl)imino}trimethylene chloride].

In the preceding example, a polymer of Formula III is synthesized in which $R_1$ and $R_2$ are each 3-hydroxypropyl. The following three examples will demonstrate how polymers of Formula III can be synthesized with $R_1$=3-hydroxypropyl and $R_2$=$CH_3$. In these examples the $R_1$ and $R_2$ constitute from 5–95% and 95%–5% respectively of the sum of $R_1+R_2$ and are distributed randomly along the polymer backbone.

EXAMPLE 9

Polymer of Formula III in which $R_1$=3-hydroxypropyl and $R_2$=$CH_3$ (Randomly distributed in a 5:95 ratio)

A solution of 462 mg. (6 milliequiv.) of poly[(methylimino)trimethylene] and 41 mg. (300μ moles) of 3-bromopropanol in 12 ml. of dimethylformamide is heated at 75° C. for 24 hours. The mixture is cooled and 2.9 g. (30 mmoles) of methyl bromide is added. The reaction mixture is heated at 50° C. for three hours. The product is isolated by concentration of the reaction mixture under reduced pressure and is washed with ether and dried under reduced pressure. Exchange of the bromide counter ion by chloride ion is accomplished in the usual manner employing an ion-exchange resin as described above.

EXAMPLE 10

Polymer of Formula III in which $R_1$=3-hydroxypropyl and $R_2$=$CH_3$ (Randomly distributed in a 50:50 ratio)

A solution of 213 mg. (3 milliequiv.) of poly[(methylimino)trimethylene] and 209 mg. (1.5 mmoles) of 3-bromopropanol is heated at 75° C. for 24 hours. The reaction mixture is cooled and 1.5 g. of methyl bromide is added. The reaction mixture is heated at 50° C. for three hours and worked up in the manner described above.

EXAMPLE 11

Polymer of Formula III in which $R_1 = 3$-hydroxypropyl and $R_2 = CH_3$ (Randomly distributed in a 95:5 ratio)

A solution of 142 mg. (2 milliequiv.) of poly[(methylimino)trimethylene] and 264 mg. (1.9 mmoles) of 3-bromopropanol is heated at 75° C. for 16 hours. After the mixture is cooled, 1 g. of methyl bromide is added and the mixture is heated at 50° C. for twelve hours. The reaction mixture is worked up in the manner described above.

EXAMPLE 12

Poly-[{Methyl-(3-methoxypropyl)imino}trimethylene Chloride]

A solution of 284 mg. (4 milliequiv.) of poly[(methylimino)trimethylene] and 2.45 g. (16 mmoles) of 3-methoxypropyl bromide in 15 ml. of dimethylformamide is heated at 75° C. for sixteen hours. The product is isolated by filtration, washed with ether and dried under reduced pressure. The product is dissolved in 25 ml. of water and the bromide counter ion is exchanged for chloride ion by ion-exchange as described above. In this manner, poly-[{methyl-(3-methoxypropyl)imino}-trimethylene chloride] is obtained.

For the synthesis of polymers of Formula III in which $R_1$ and $R_2$ are 3-methoxypropyl and methyl respectively in ratios varying from 5:95 to 95:5, the procedure is essentially as described above in which the poly-[(methylimino)trimethylene] is reacted with a limiting amount of 3-methoxypropyl bromide and then with an excess of methyl bromide.

EXAMPLE 13

Poly-[{Methyl-(3-methylthiopropyl)imino}trimethylene Chloride]

A solution of 426 mg. (6 milliequiv.) of poly[(methylimino)trimethylene] and 4.06 g. of 3-methylthiopropyl bromide in 15 ml. of dimethylformamide is heated at 75° C. for 24 hours. The product is isolated by filtration, taken up in 30 ml. of water and passed through a column of 45 ml. of Dowex 1-X2 ion-exchange resin (36 mmoles chloride ion). Concentration of the aqueous eluate yields poly[{methyl-(3-methylthiopropyl)imino}-trimethylene chloride].

For the synthesis of polymers of Formula III in which $R_1$ and $R_2$ are 3-methylthiopropyl and methyl respectively in ratios varying from 5:95 to 95:5, the procedure is essentially as described above in which the poly-[(methylimino)trimethylene] is reacted with a limiting amount of 3-methylthiopropyl bromide and then with an excess of methyl bromide.

EXAMPLE 14

Poly-[{Methyl-(3-ammoniopropyl)imino}trimethylene Dichloride]

A solution of 568 mg. (8 milliequiv.) of poly[(methyliminio)trimethylene] and 8.6 g. (30 mmoles) of 3-phthalimidopropyl bromide in 25 ml. of dimethylformamide is heated at 75° C. for eighteen hours. The product is isolated by filtration, suspended in 10 ml. of methanol and treated with 1 g. of anhydrous hydrazine at 50° C. for three hours. The mixture is concentrated at reduced pressure, acidified with dilute HCl, again concentrated at reduced pressure, triturated with ether and isolated by filtration. The product is taken up in water and passed through a 45 ml. column of Dowex 1-X2 ion-exchange resin (36 mmoles chloride). Concentration of the aqueous eluate yields poly-[{methyl-(3-ammoniopropyl)iminio}trimethylene dichloride].

Alternatively, a solution of 568 mg. (8 milliequiv.) of poly-[(methylimino)trimethylene] and 6.3 g. (40 mmoles) of 1-bromo-3-chloropropane in 20 ml. of dimethylformamide is heated at 75° C. for eighteen hours. The reaction mixture is concentrated under reduced pressure and heated with 30 ml. of liquid ammonia at 50° C. for five hours. The ammonia is allowed to evaporate, and the product is converted to the chloride-ion containing form by passage through a 45 ml. column of Dowex 1-X2 ion-exchange resin on the chloride ion cycle.

For the synthesis of polymers of Formula III in which $R_1$ and $R_2$ are 3-ammoniopropyl and methyl respectively in ratios varying from 5:95 to 95:5, the procedure is essentially as described above in which the poly-[(methylimino)trimethylene] is reacted with a limiting amount of either 3-phthalimidopropyl bromide or 1-bromo-3-chloropropane and then with an excess of methyl bromide.

EXAMPLE 15

Poly-[{Methyl-(3-methylammoniopropyl)imino}-trimethylene Dichloride]

A solution of 710 mg. (10 milliequiv.) of poly[(methylimino)trimethylene] and 8 g. of 1-bromo-3-chloropropane in 30 ml. of dimethylformamide is heated at 75° C. for 16 hours. The mixture is concentrated under reduced pressure, suspended in 10 ml. of methanol and treated with 3 g. of methylamine at 50° C. in a sealed tube. The reaction mixture is concentrated under reduced pressure, taken up in water and passed through a 50 ml. column of Dowex 1-X2 ion exchange resin to yield the desired product.

For the synthesis of polymers of Formula III in which $R_1$ and $R_2$ are 3-methylammoniopropyl and methyl respectively in ratios varying from 5:95 to 95:5, the procedure is essentially the same as described above in which the poly-[(methylimino)trimethylene] is first reacted with a limiting amount of 1-bromo-3-chloropropane and then with an excess of methyl bromide.

EXAMPLE 16

Poly-[{Methyl-(3-dimethylammoniopropyl)imino}-trimethylene Dichloride]

A solution of 710 mg. (10 milliequiv.) of poly[(methylimino)trimethylene] and 7.9 g. of 1-bromo-3-chloropropane in 35 ml. of dimethylformamide is heated at 75° C. for sixteen hours. The mixture is concentrated under reduced pressure, suspended in 10 ml. of methanol and treated with 2.3 g. (50 mmoles) of dimethylamine at 50° C. in a sealed tube. The reaction mixture is concentrated under reduced pressure, taken up in water and passed through a 50 ml. column of Dowex 1-X2 ion exchange resin (40 mmoles of chloride ion) yielding poly-[{methyl-(3-dimethylammoniopropyl)imino}trimethylene dichloride].

For the synthesis of polymers of Formula III in which $R_1$ and $R_2$ are 3-dimethylammoniopropyl and methyl respectively in ratios varying from 5:95 to 95:5 the procedure is essentially as described above in which the poly[(methylimino)trimethylene] is treated with a limiting amount of 1-bromo-3-chloropropane.

EXAMPLE 17

Poly-[{Methyl-(3-trimethylammoniopropyl)imino}-trimethylene Dibromide]

A solution of 710 mg. (10 milliequiv.) of poly[(methylimino)trimethylene] and 10.4 g. (40 mmoles) of 3-bromopropyltrimethylammonium bromide in 40 ml. of purified dimethylformamide is heated at 75° C. for twelve hours. The product is isolated by filtration, washed with acetone and dried under reduced pressure, yielding 1.8 g. of poly-[{methyl-(3-trimethylammoniopropyl)imino}trimethylene dibromide].

EXAMPLE 18

Poly-[{Methyl-(3-trimethylammoniopropyl)imino}-trimethylene Dichloride]

A solution of 1.66 g. (5 milliequiv.) of poly-[{methyl-(3-trimethylammoniopropyl)imino}trimethylene dibromide] in 85 ml. of water is passed slowly through a column containing 50 ml. (40 mmoles) of Dowex 1-X2 resin on the chloride ion cycle. Water is then passed through until no chloride ion can be detected in the eluate. Concentration of the combined eluate to dryness at 50° C. yields poly-[{methyl-(3-trimethylammoniopropyl)imino}trimethylene dichloride].

For the synthesis of polymers of Formula III in which $R_1$ and $R_2$ are 3-trimethylammoniopropyl and methyl respectively in ratios varying from 5:95 to 95:5, the procedure is essentially as described above in Example 17 in which the poly-[(methylimino)trimethylene] is reacted with a limiting amount of 3-bromopropyltrimethylammonium bromide and then with an excess of methyl bromide.

EXAMPLE 19

Poly-[{Methyl-(carboethoxymethyl)imino}trimethylene Chloride]

A solution of 1 g. (14 milliequiv.) of poly-[(methylimino)trimethylene] and 8.8 g. (56 mmoles) of ethyl α-bromoacetate in 20 ml. of dimethylformamide is heated at 50° C. for twelve hours. The mixture is diluted with five volumes of ether and the product is isolated by filtration. The product is taken up in water and passed through a 75 ml. column of Dowex 1-X2 ion-exchange resin (60 mmoles chloride ion) and the eluate is concentrated under reduced pressure to yield poly-[{methyl-(carboethoxymethyl)imino}trimethylene chloride].

EXAMPLE 20

Poly-[{Methyl-(carbamylmethyl)imino}trimethylene Chloride]

A solution of 355 mg. (5 milliequiv.) of poly-[(methylimino)trimethylene] and 3.5 g. (25 mmoles) of 2-bromoacetamide in 10 ml. of dimethylformamide is heated at 60° C. for 15 hours. The product is isolated by filtration, taken up in water and passed through a 25 ml. column of Dowex 1-X2 ion exchange resin (20 mmoles chloride ion) yielding poly-[{methyl-(carbamylmethyl)imino}trimethylene chloride].

For polymers of Formula III in which $R_1$ and $R_2$ are carbamylmethyl and methyl respectively in ratios varying from 95:5 to 5:95, the procedure is essentially as described above in which the poly-[(methylimino)-trimethylene] is treated first with a limiting amount of 2-bromoacetamide and then with an excess of methyl bromide.

EXAMPLE 21

Poly-[{Methyl-(2-oxopropyl)imino}trimethylene Chloride]

A solution of 355 mg. (5 milliequiv.) of poly-[(methylimino)trimethylene] and 2.3 g. (25 mmoles) of chloropropanone-2 is heated at 50° C. for 16 hours. The product is isolated by filtration, triturated with ether and dried under reduced pressure.

For polymers of Formula III in which $R_1$ and $R_2$ are 2-oxopropyl and methyl respectively in ratios varying from 95:5 to 5:95, the procedure described above is followed in which the poly-[(methylimino)trimethylene] is treated first with a limiting amount of chloropropanone-2 and then with an excess of methyl bromide. Treatment of the product with Dowex 1-X2 on the chloride ion cycle gives the product containing the chloride ion exclusively.

EXAMPLE 22

Poly-[{Methyl-(benzyl)imino}trimethylene Chloride]

A solution of 710 mg. (10 milliequiv.) of poly-[(methylimino)trimethylene] and 6.8 g. (40 mmoles) of benzyl bromide in 15 ml. of dimethylformamide is heated at 50° C. for 16 hours. The product is isolated by concentration of the reaction mixture under reduced pressure and extraction into water. The aqueous solution is passed through a 25 ml. column of Dowex 1-X2 ion exchange resin (40 mmoles of chloride ion) yielding the desired product containing the chloride counter ion.

For polymers of Formula III in which $R_1$ and $R_2$ are benzyl and methyl respectively, the procedure described above is followed in which the poly-[(methylthio)trimethylene] is first reacted with a limited amount of benzyl bromide and then an excess of methyl bromide.

EXAMPLE 23

Poly-[{Methyl-(1-propen-3-yl)imino}trimethylene Chloride]

A solution of 420 mg. (6 milliequiv.) of poly-[(methylimino)trimethylene] and 3.7 g. (30 mmoles) of 3-bromopropene-1 (allyl bromide) in 12 ml. of dimethylformamide is heated at 50° C. for 16 hours. The product is isolated by filtration and dissolved in water. The aqueous solution is passed through a 40 ml. column of Dowex 1-X2 ion exchange resin (32 mmoles of chloride ion) and the eluate is concentrated under reduced pressure yielding the desired product containing the chloride counter ion.

For compounds of Formula III in which $R_1$ and $R_2$ are 1-propen-3-yl and methyl respectively in ratios varying from 95:5 to 5:95, the procedure is similar to that described above in which the poly-[(methylimino)-trimethylene] is reacted with a limiting quantity of 3-bromopropene-1 and then an excess of methyl bromide.

EXAMPLE 24

Poly-[{Methyl-(1-propyn-3-yl)imino}trimethylene Chloride]

A solution of 710 mg. (10 milliequiv.) of poly-[(methylimino)trimethylene] and 3.6 g. (30 mmoles) of 3-bromopropyne-1 (propargyl bromide) in 12 ml. of dimethylformamide is heated at 50° C. for 16 hours. The product is isolated by filtration, dissolved in water and passed through a 40 ml. column of Dowex exchange resin (32 mmoles of chloride ion) yielding the desired product containing the chloride counter ion.

As for previous examples, polymers of Formula III in which $R_1$=1-propyn-3-yl and $R_2$=$CH_3$ in ratios ranging from 5:95 to 95:5 are synthesized by first treating the poly-[(methylimino)trimethylene] with a limiting amount of propargyl bromide and then with an excess of methyl bromide.

EXAMPLE 25

Poly-[{Methyl-(3-trimethylammoniopropyl)imino}-trimethylene Dichloride]

A mixture of 32.1 g. (0.30 equiv.) of poly-[(methylimino)trimethylene hydrochloride], 217 g. (0.83 equiv.) of 3-bromopropyltrimethylammonium bromide, 12.0 g. (0.30 equiv.) of sodium hydroxide, and 96 ml. of water is agitated until complete solution is achieved. The mixture is allowed to stand at room temperature for seven days. Next, the mixture is stirred while 1800 ml. of acetonitrile is added at the rate of 30 ml./min. The product precipitates and the acetonitrile phase is decanted from the product. Next, the product is washed twice with one liter of a mixture containing 5% water and 95% acetonitrile and finally with 150 ml. of acetonitrile. After the product is dried in vacuo, a 107.5 g. residue is obtained.

The product is taken up in 1135 ml. of water, placed on an Amicon filter cell and desalted by using a UM-2 Diaflo ® ultrafilter under 60 lbs. of nitrogen pressure.

After the halide-ion test of the filtrate becomes negative, the combined retentates are concentrated under reduced pressure yielding 85 g. of poly-[{methyl-(3-trimethylammoniopropyl)imino}trimethylene dibromide].

The above product is dissolved in 2300 ml. of water and passed slowly through a 2000 ml. column of AG1 X-2 ion exchange resin (0.8 milliequiv. Cl⁻/ml.) at the rate of 7 ml./min. The combined effluents are then concentrated at 50° C. under reduced pressure yielding 66 g. of poly-[{methyl-(3-trimethylammoniopropyl)imino}trimethylene dichloride].

Various changes and modifications may be made in carrying out the present invention without departing from the spirit and scope thereof. Insofar as these changes and modifications are within the purview of the annexed claims, they are to be considered as part of this invention.

What is claimed is:

1. A method of preparing a linear, unbranched, non-cross-linked polymer comprising repeating units of the formula

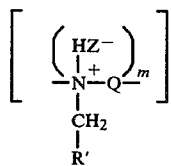

where m is the integer 1 or 0, R' is hydrogen, loweralkyl, phenyl, naphthyl, or naphthylethyl, Q is trimethylene and $Z^-$ is a counter anion comprising reacting a polymer comprising repeating units of the formula

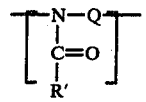

where R' and Q are as previously defined with at least a molar equivalent of a chemical reductant, and where m is 1 adding mineral acid HZ.

2. A method according to claim 1 where the chemical reductant is diborane.

3. A method of preparing a linear unbranched non-cross-linked polymer comprising repeating units of the formula

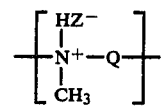

where Q is trimethylene, and $Z^-$ is a counteranion comprising admixing a polymer comprising repeating units of the formula

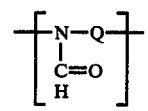

where Q is trimethylene with more than one equivalent each of formaldehyde and formic acid and heating the resulting admixture at a temperature of from 30° to 100° C. for up to 100 hours and adding mineral acid HZ.

4. A method according to claim 3 where a mixture of 97 to 100% formic acid and aqueous formaldehyde is employed and, followed the heating of said admixture, there is then added to the reaction mixture an aqueous mineral acid HZ, and the aqueous acidic mixture is subjected to distillation under reduced pressure thereby removing reagents and by-products.

5. A method of preparing a linear unbranched non-cross-linked polymer comprising repeating units of the formula

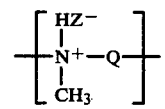

where Q is trimethylene and $Z^-$ is a counteranion comprising admixing a polymer comprising repeating units of the formula

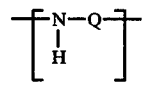

with an excess of formaldehyde and formic acid, and heating the resulting admixture to a temperature of from 30° to 100° C. for up to 100 hours wherein a mixture of 97 to 100% formic acid and aqueous formaldehyde is employed and, following the heating of said admixture, there is then added to the reaction mixture an aqueous mineral acid HZ, and the aqueous acidic mixture is subjected to distillation under reduced pressure thereby removing reagents and by-products.

6. A method for making a first linear, unbranched non-cross-linked polymer comprising repeating units of the formula

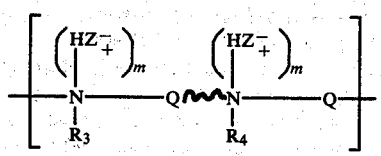

where $Z^-$ is a counteranion, Q is trimethylene, m is the integer 0 or 1, ⁓ indicates bonding to a plurality of the groups

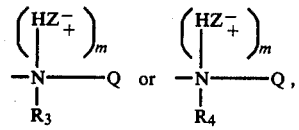

where $Z^-$, Q, and m are as previously defined and $R_3$ and $R_4$ are the same or different and are loweralkyl; monohydroxy-substituted loweralkyl, polyhydroxy substituted $C_3$ to $C_6$ alkyl and polyhydroxy-substituted $C_3$ to $C_6$ cycloalkyl; $C_3$ to $C_7$ cycloalkyl; $C_3$ to $C_7$ cycloalkyl substituted loweralkyl; loweralkyl-substituted $C_3$ to $C_7$ cycloalkyl; ammonioloweralkyl; loweralkylammonioloweralkyl; diloweralkylammonioloweralkyl; triloweralkylammonioloweralkyl; carboxyloweralkyl; carboloweralkoxyloweralkyl; $C_3$ to $C_7$ alkenyl; $C_3$ to $C_7$ alkynyl; aralkyl; carbamyloweralkyl; fluoroloweralkyl; cyanoloweralkyl; guanidinoloweralkyl; carbamidinoloweralkyl; N-loweralkylcarbamidinoloweralkyl; loweralkoxyloweralkyl; loweralkylthioloweralkyl; furanosyl; pyranosyl; and loweralkanoylloweralkyl; comprising reacting a second polymer comprising repeating units of the formula

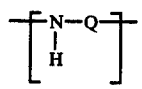

where Q is as previously defined with: (a) when $R_3$ and $R_4$ are alike, at least 1.5 equivalents of RX where R is $R_3$ or $R_4$ and X is halide or sulfonate, sulfate in an inert solvent at a temperature of from 30° C. to 100° C. and (b) when $R_3$ and $R_4$ are different, first reacting the second polymer with less than an equivalent of $R_3X$ in an inert solvent followed by reacting with an amount of a base which is matching to the equivalents of $R_3X$ employed to form a third polymer; then reacting said third polymer in an inert solvent with a reactant $R_4X$ such that the amounts of $R_3X$ and $R_4X$ employed are substantially equivalent to the equivalents of repeating formula units in said second polymer.

7. A method for making a first linear, unbranched non-cross-linked polymer comprising repeating units of the formula

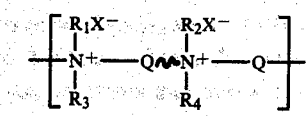

where $X^-$ is a halide, sulfate or sulfonate, Q is trimethylene, and ⁓ indicates bonding to a plurality of the groups

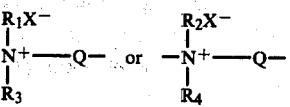

where $X^-$ and Q are as previously defined and $R_3$ and $R_4$ are the same or different and are loweralkyl; monohydroxy-substituted loweralkyl, polyhydroxy substituted $C_3$ to $C_6$ alkyl and polyhydroxy-substituted $C_3$ to $C_6$ cycloalkyl; $C_3$ to $C_7$ cycloalkyl; $C_3$ to $C_7$ cycloalkyl-substituted loweralkyl; loweralkyl substituted $C_3$ to $C_7$ cycloalkyl; ammonioloweralkyl; loweralkylammonioloweralkyl; diloweralkylammonioloweralkyl; triloweralkylammonioloweralkyl; carboxyloweralkyl; carboloweralkoxyloweralkyl; $C_3$ to $C_7$ alkenyl; $C_3$ to $C_7$ alkynyl; aralkyl; carbamyloweralkyl; fluoroloweralkyl; cyanoloweralkyl; guanidinoloweralkyl; carbamidinoloweralkyl; N-loweralkylcarbamidinoloweralkyl; loweralkoxyloweralkyl; loweralkylthioloweralkyl; furanosyl; pyranosyl; and loweralkanoylloweralkyl; and $R_1$ and $R_2$ are the same or different and are hydrogen, loweralkyl; monohydroxy-substituted loweralkyl, polyhydroxy-substituted $C_3$ to $C_6$ alkyl and polyhydroxy-substituted $C_3$ to $C_6$ cycloalkyl; $C_3$ to $C_7$ cycloalkyl; $C_3$ to $C_7$ cycloalkyl-substituted loweralkyl; loweralkyl-substituted $C_3$ to $C_7$ cycloalkyl; ammonioloweralkyl, loweralkylammonioloweralkyl; diloweralkylammonioloweralkyl; triloweralkylammonioloweralkyl; carboxyloweralkyl; carboloweralkoxyloweralkyl; $C_3$ to $C_7$ alkenyl; $C_3$ to $C_7$ alkynyl; aralkyl; carbamylloweralkyl; fluoroloweralkyl; cyanoloweralkyl; guanidinoloweralkyl; carbamidinoloweralkyl; N-loweralkylcarbamidinoloweralkyl; loweralkoxyloweralkyl; loweralkylthioloweralkyl; furanosyl; pyranosyl; and loweralkanoylloweralkyl; comprising reacting a second polymer comprising repeating units of the formula

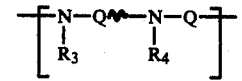

where $R_3$, $R_4$, and Q are as previously defined and ⁓ indicates bonding to a plurality of the groups

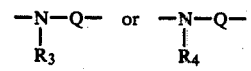

with:
(a) when $R_1$ and $R_2$ are alike at least an equivalent of RX where R is $R_1$ and X is halide, sulfonate or sulfate;
(b) when $R_1$ is different from $R_2$, reacting the second polymer first with from 5 to 95% of one equivalent of $R_1X$, followed by reacting with at least one equivalent of $R_2X$.

8. A method according to claim 7 wherein $R_1$ or $R_2$ are ammonioalkyl; loweralkylammonioloweralkyl; diloweralkylammonioloweralkyl; and triloweralkylammonioloweralkyl where said ammonio cation is countered with an anion $Z^-$.

9. A method according to claim 7 where $R_1$ or $R_2$ are hydroxy-substituted loweralkyl and hydroxy substituted cycloloweralkyl.

10. A method according to claim 7 where $R_3$ and $R_4$ are methyl, and said first polymer is poly-[{methyl-(3-trimethylammoniopropyl)iminio}trimethylene dichloride].

11. A method according to claim 7 where $R_3$ and $R_4$ are methyl, and said first polymer is poly-[{(methyl-(3-hydroxypropyl)iminio}trimethylene chloride].

12. A method according to claim 7 where $R_3$ and $R_4$ are methyl, and said first polymer is poly-[{methyl-(3-methoxypropyl)iminio}trimethylene chloride].

13. A method according to claim 7 where $R_3$ and $R_4$ are methyl, and said first polymer is poly-[{methyl-(2-oxopropyl)iminio}trimethylene chloride].

14. A method according to claim 7 where $R_3$ and $R_4$ are methyl, and said first polymer is poly-[{methyl(carboethoxymethyl)iminio}trimethylene chloride].

15. A method according to claim 7 where $R_1$, $R_2$, $R_3$ and $R_4$ are methyl.

* * * * *

UNITED STATES PATENT AND TRADEMARK OFFICE
CERTIFICATE OF CORRECTION

PATENT NO. : 4,206,295
DATED : June 3, 1980
INVENTOR(S) : ARTHUR F. WAGNER ET AL.

It is certified that error appears in the above-identified patent and that said Letters Patent are hereby corrected as shown below:

In the structures at:

Col. 2, between lines 2-10 and 54-60
    Col. 3, between lines 30-36, 39-45, 50-57 and 60-65
    Col. 5, between lines 25-33, and 60-68
    Col. 6, between lines 27-35
    Col. 7, between lines 23-30
    Col. 21, between lines 5-15 and 20-25 those portions which read $(R_1 Z_+^-)_m$ $(R_2 Z_+^-)_m$ should read $(R_1 Z^-{}_+)_m$ $(R_2 Z^-{}_+)_m$ and those which read $(HZ_+^-)_m$ should read $(HZ^-{}_+)_m$ Signed and Sealed this Twenty-eighth Day of October 1980

[SEAL]

Attest:

*Attesting Officer*

SIDNEY A. DIAMOND

*Commissioner of Patents and Trademarks*